(12) United States Patent
Min et al.

(10) Patent No.: US 11,297,449 B2
(45) Date of Patent: Apr. 5, 2022

(54) COCHLEAR EXTERNAL DEVICE WITH EXTERNAL MICROPHONE

(71) Applicant: TODOC Co., Ltd., Seoul (KR)

(72) Inventors: Kyou-Sik Min, Gyeonggi-do (KR); Woojin Ahn, Seoul (KR)

(73) Assignee: TODOC CO., LTD., Seoul (KR)

( * ) Notice: Subject to any disclaimer, the term of this patent is extended or adjusted under 35 U.S.C. 154(b) by 0 days.

(21) Appl. No.: 16/999,150

(22) Filed: Aug. 21, 2020

(65) Prior Publication Data
US 2021/0058718 A1 Feb. 25, 2021

(51) Int. Cl.
*H04R 25/00* (2006.01)
*A61N 1/36* (2006.01)

(52) U.S. Cl.
CPC .......... *H04R 25/556* (2013.01); *H04R 25/43* (2013.01); *H04R 25/606* (2013.01); *A61N 1/36038* (2017.08); *H04R 2225/0213* (2019.05)

(58) Field of Classification Search
CPC ................ H04R 2460/13; H04R 1/105; H04R 2225/021
USPC .................................................. 381/326, 330
See application file for complete search history.

(56) References Cited

U.S. PATENT DOCUMENTS

| | | | | |
|---|---|---|---|---|
| 4,606,329 A | * | 8/1986 | Hough | H04R 25/606 381/326 |
| 6,631,197 B1 | * | 10/2003 | Taenzer | H04R 25/606 381/326 |
| 7,142,926 B2 | * | 11/2006 | Crawford | H04R 25/606 607/55 |
| 7,496,206 B2 | * | 2/2009 | Husung | H04R 25/554 381/326 |
| 7,889,879 B2 | * | 2/2011 | Dillon | A61N 1/36038 381/326 |
| 8,699,734 B1 | | 4/2014 | Haller | |
| 8,811,643 B2 | | 8/2014 | Crawford et al. | |
| 2005/0251225 A1 | | 11/2005 | Faltys et al. | |

(Continued)

FOREIGN PATENT DOCUMENTS

JP 2017-225074 A 12/2017
WO WO 2020/023011 A1 1/2020

OTHER PUBLICATIONS

European Search Report For EP 20192154.1 dated Apr. 20, 2021 from European patent office in a counterpart European patent application.

(Continued)

*Primary Examiner* — Suhan Ni
(74) *Attorney, Agent, or Firm* — The PL Law Group, PLLC

(57) ABSTRACT

A cochlear external device with an external microphone according to an embodiment of the present disclosure may include an external device body attached to a side of the head of a user, an internal microphone embedded in the external device body to collect sound, an external microphone located at the outside of the external device body to be attached around the ear of the user to collect sound, a connection cable configured to connect the external microphone and the external device body in a wired manner; and a control unit embedded in the external device body to generate an output signal based on the sound collected by at least one of the internal microphone and the external microphone and transmit the generated output signal to a cochlear implant transplanter.

7 Claims, 6 Drawing Sheets

(56) References Cited

U.S. PATENT DOCUMENTS

| | | |
|---|---|---|
| 2007/0016267 A1 | 1/2007 | Griffin et al. |
| 2010/0137942 A1 | 6/2010 | Darley et al. |
| 2011/0319703 A1 | 12/2011 | Wiskerke et al. |
| 2013/0006327 A1 | 1/2013 | Mishra et al. |
| 2016/0256688 A1 | 9/2016 | Kasic et al. |
| 2016/0317810 A1 | 11/2016 | Crawford et al. |

OTHER PUBLICATIONS

Examination Report dated Mar. 1, 2021 from Australia Intellectual Property Office in a counterpart Australian Patent Application No. 2020220189.

* cited by examiner (a)

(b)

(a)

(b)

(a)

(b)

(c)

COCHLEAR EXTERNAL DEVICE WITH EXTERNAL MICROPHONE

CROSS-REFERENCE TO RELATED APPLICATION AND CLAIM OF PRIORITY

This application claims priority to Korean Patent Applications No. 10-2019-0102645 filed on Aug. 21, 2019 in the Korean Intellectual Property Office (KIPO), the entire disclosures of which are incorporated by reference herein in their entirety.

GOVERNMENT LICENSE RIGHTS

This invention was made with Korean government support under the Korea Health Technology R&D Project awarded by the Korea Health Industry Development Institute (KHIDI), funded by the Ministry of Health & Welfare, Republic of Korea (grant number: HI20C0954000020). The government has certain rights in the invention."

BACKGROUND

1. Technical Field

This disclosure relates to a cochlear external device with an external microphone.

2. Background Art

A cochlear implant is a device that directly provides electrical stimulation to the remaining auditory nerves of a patient who cannot hear sound due to damage to the cochlea, and may include a transplanter inserted into the human body to provide electrical stimulation to the auditory nerve and an external device for collecting and processing sound into signals from the outside of the human body to provide the signals to the transplanter.

Here, the external device may be classified into an earring type hanging on the ear, an integral type attached to the back of the head, and the like. However, the integral type cochlear external device is lost frequently by a user, and a separate fixing device is always required to attach the integral type cochlear external device to the back of the head of the user.

Meanwhile, the cochlear external device has a microphone for collecting sound, but the microphone has a limit in its sound-receiving power. In particular, if the cochlear implant is worn on only one ear, it is difficult to collect sound at the other side, so that the sound cannot be heard well.

Therefore, there is a demand in the art to overcome the limitations of the conventional integral type cochlear external device.

SUMMARY

To solve the problem, an embodiment of the present disclosure provides a cochlear external device with an external microphone.

The cochlear external device with an external microphone may include: an external device body attached to a side of the head of a user; an internal microphone embedded in the external device body to collect sound; an external microphone located at the outside of the external device body to be attached around the ear of the user to collect sound; a connection cable configured to connect the external microphone and the external device body in a wired manner; and a control unit embedded in the external device body to generate an output signal based on the sound collected by at least one of the internal microphone and the external microphone and transmit the generated output signal to a cochlear implant transplanter.

The external microphone may be provided in a hook type that hangs on the earflap of the user or in a terminal type that is attached around the ear of the user.

At this time, the external microphone may include: a microphone body provided in a hook type or a terminal type; and a microphone element embedded in the microphone body to collect sound, and may further include a telecoil embedded in the microphone body to collect sound instead of the microphone element.

The connection cable may be detachably attached to the external device body.

The cochlear external device may further include a power supply unit having a battery for performing a power charging/discharging operation and configured to generate and supply a driving power for the cochlear external device by using a battery charge power.

In addition, the cochlear external device may further include a contact sensor configured to sense whether the external device body is attached to the head of the user and notify the sensing result, and the control unit may change an operation mode according to the sensing result of the contact sensor.

Also, the cochlear external device may further include a vibration sensor configured to sense a user touch pattern based on vibration and notify the sensing result, and the control unit may change an operation mode according to the sensing result of the vibration sensor.

The external device body may include: a lower body having an inner space for supporting components to be embedded therein; an inner cover having a magnet insert hole and a microphone sound penetration hole and configured to cover an upper side of the lower body; a magnet inserted into the magnet insert hole and configured to have an adjustable height; and an outer cover configured to entirely cover and fully seal the inner cover into which the magnet is inserted.

Moreover, all features of the present disclosure are not limited above. Various features of the present disclosure and their advantages and effects may be understood in more detail with reference to the following specific embodiments.

According to an embodiment of the present disclosure, it is possible to overcome the limitations of the conventional integral type cochlear external device so that the cochlear external device is not easily lost without using a separate fixing device and the microphone has an improved sound-receiving power.

DETAILED DESCRIPTION OF THE EMBODIMENTS

Figure 1:
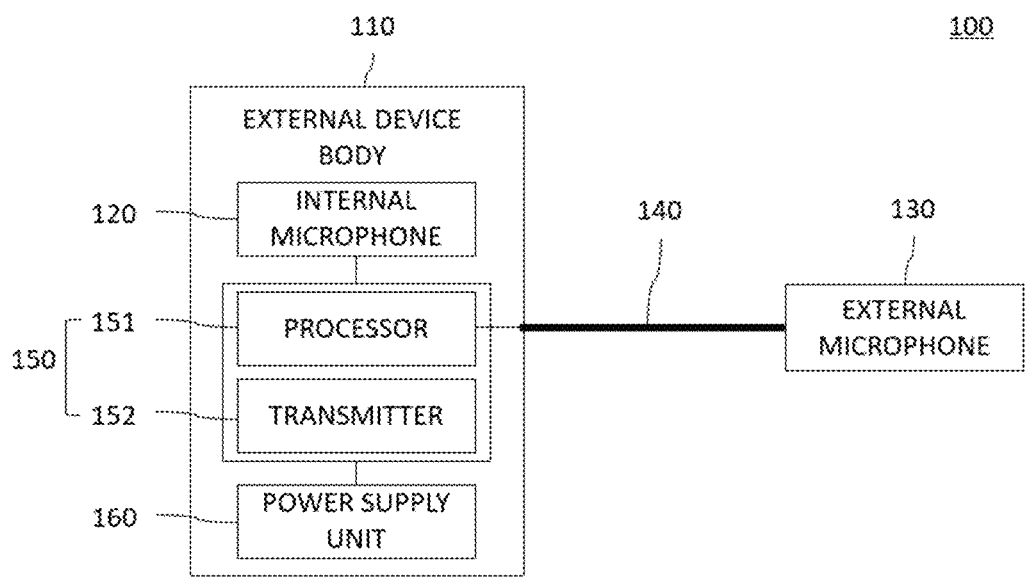
FIG. 1 is a block diagram showing a cochlear external device with an external microphone according to an embodiment of the present disclosure.

Hereinafter, a preferred embodiment will be described in detail with reference to the accompanying drawings so that a person having ordinary knowledge in the art can easily implement the present disclosure. However, in describing the preferred embodiment of the present disclosure in detail, if it is determined that a detailed description of a related known function or configuration may unnecessarily obscure the subject matter of the present disclosure, the detailed description thereof will be omitted. In addition, the same reference numerals are used throughout the drawings for components having similar functions and operations.

Moreover, throughout the specification, when a part is said to be 'connected' with another part, this encompasses not only a case where these parts are 'directly connected', but also a case where these parts are 'indirectly connected' with another element being interposed therebetween. In addition, 'including' a certain component means that other components may be further included, rather than excluding other components unless specifically stated to the contrary.

FIG. 1 is a block diagram showing a cochlear external device with an external microphone according to an embodiment of the present disclosure.

Referring to FIG. 1, a cochlear external device 100 with an external microphone according to an embodiment of the present disclosure may include an external device body 110, an internal microphone 120, an external microphone 130, a connection cable 140, a control unit 150, and a power supply unit 160.

The external device body 110 is implemented to be attached to a side of the head of a user and provides an internal space in which the internal microphone 120 and the control unit 150 are embedded.

The internal microphone 120 may be embedded in the external device body 110 and collect external sound (especially sound around the side of the head of the user).

The external microphone 130 may be located outside the external device body 110 to be attached around the ear canal of the user and may collect external sound (especially, sound around the ear of the user).

The connection cable 140 may connect the external device body 110 and the external microphone 130 in a wired manner. At this time, the connection cable 140 is preferably implemented to be detachably attached to the external device body 110 by additionally including any one of various data terminals such as a 5-pin terminal, a C-type terminal and an Apple 8-pin terminal as a microphone.

In addition, a groove for accommodating the connection cable 140 therein may be formed along the circumference of a side surface of the external device body 110. In this case, one end of the connection cable 140 may be connected to a point of the groove formed at the side surface of the external device body 110 so as to be folded and unfolded.

The control unit 150 has a processor 151 and a transmitter 152 embedded in the external device body, and generates a signal for transmission to a cochlear implant transplanter based on the sound collected by at least one of the internal microphone 120 and the external microphone 130 and then transmits the generated sound to the cochlear implant transplanter.

The processor 151 may generate a signal to be transmitted to the cochlear implant transplanter (not shown) by processing the sound collected from at least one of the internal microphone 120 and the external microphone 130.

For example, if the external microphone 130 is connected to the external device body 110 through the connection cable 140, the processor 151 may generate and output a signal for transmission to the cochlear implant transplanter using only the external microphone 130. If the external microphone 130 is not connected, the processor 151 may be implemented to use only the internal microphone 120 instead of the external microphone 130.

Alternatively, even when the connection cable 140 is connected, it is possible to use both the internal microphone 120 and the external microphone 130 so that a signal is generated by synthesizing two sounds or a signal is generated by selecting a sound with higher quality among the two sounds. In this case, the sound quality may be determined based on a signal level, SNR, or the like.

The transmitter 152 may transmit the signal generated by the control unit 150 to the cochlear implant transplanter (not shown). For example, the transmitter 152 may be implemented as a transmission coil to transmit the signal to a reception coil included in the cochlear implant transplanter (not shown).

The power supply unit 160 includes a battery capable of performing a power charging/discharging operation, and generates and supplies a driving power for the cochlear external device by using a battery charging power.

Figure 2:
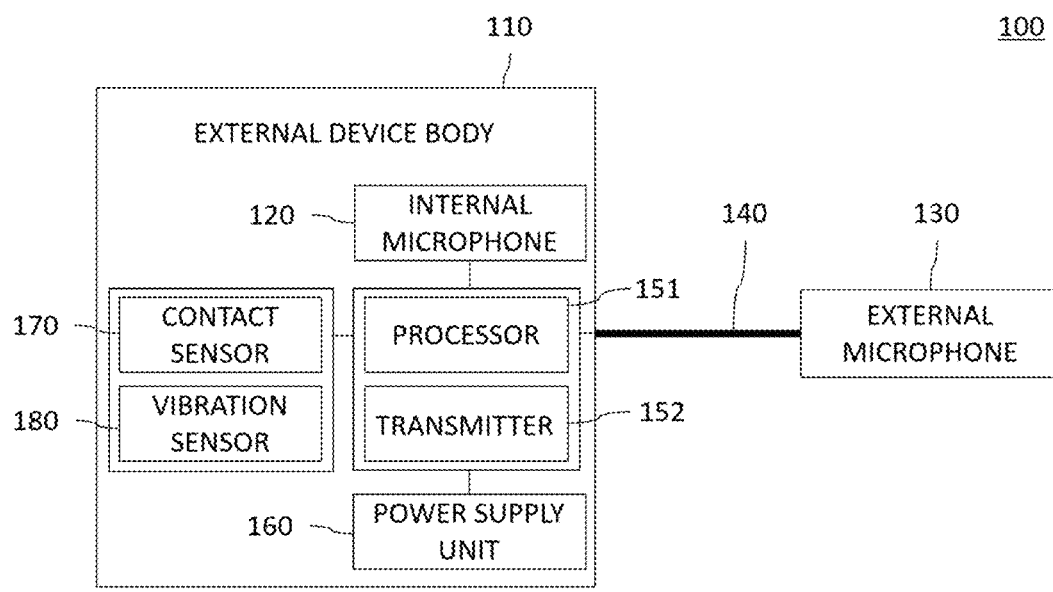
FIG. 2 is a block diagram showing the cochlear external device with an external microphone according to another embodiment of the present disclosure.

FIG. 2 is a block diagram showing the cochlear external device with an external microphone according to another embodiment of the present disclosure.

As shown in FIG. 2, the cochlear external device of the present disclosure may further include at least one of a contact sensor 170 and a vibration sensor 180 embedded in the external device body 110 in addition to the components of FIG. 1.

The contact sensor 170 senses whether the external device body 110 is attached to the head of the user, namely the side of the head, and notifies the sensing result. The contact sensor 170 may sense the contact based on temperature, capacitance, magnetic force, or the like, but the sensing method may be changed in various ways in the future.

Then, the processor 151 may adjust an operation mode of the cochlear external device according to the sensing result of the contact sensor 170.

For example, if the contact sensor 170 senses and notifies that the external device body is attached, the operation mode of the cochlear external device is switched from a sleep mode to a wake-up mode so that a sound collecting and transmitting operation may be performed.

Meanwhile, if the contact sensor 170 senses and notifies that the external device body is detached, the operation mode of the cochlear external device is switched again to the sleep mode so that the above sound collecting and transmitting operation may be stopped.

That is, since the cochlear external device is operated only while the user attaches the cochlear external device to the head for use of the cochlear implant, unnecessary power consumption may be prevented in advance.

The vibration sensor 180 may sense whether a user touches or not based on vibration and output the sensing result.

Then, the processor 151 may define a user control value corresponding to the user touch pattern in advance, and based on this, may change the operation mode of the cochlear external device according to the sensing result of the vibration sensor 180.

For example, if the cochlear external device is in the sleep mode, the operation mode of the cochlear external device may be immediately switched to the wake-up mode when the user taps the external device body.

Figure 3:
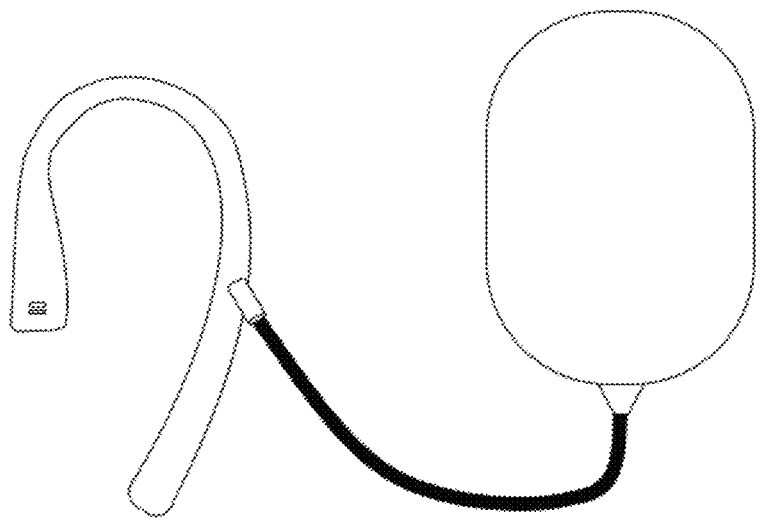
FIGS. 3 and 4 are diagrams showing an appearance of the external microphone according to embodiments of the present disclosure.
Figure 3:
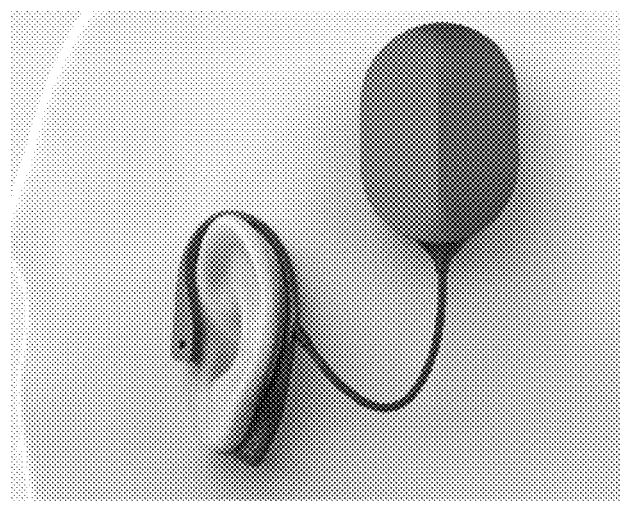
Figure 4:
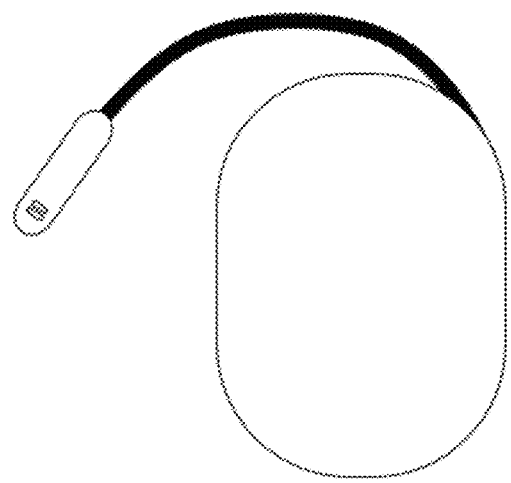
Figure 4:
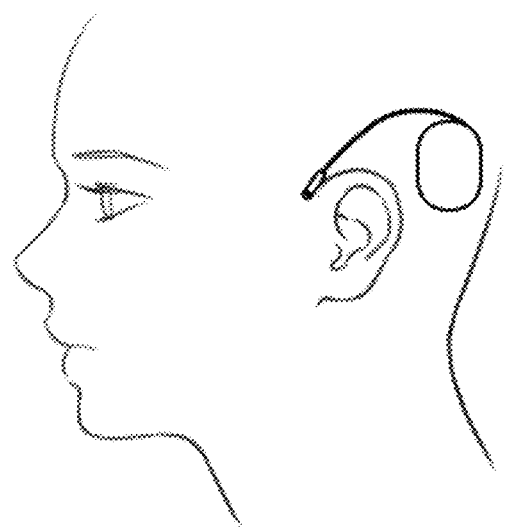

FIGS. 3 and 4 are diagrams showing an appearance of the external microphone according to embodiments of the present disclosure.

The external microphone 130 of the present disclosure may be implemented in a hook type that hangs on the earflap of the user as shown in FIG. 3 or may be implemented in a terminal type that is attached around the ear of the user as shown in FIG. 4. Both of them may be detachably attached to the external device body 110 by means of the connection cable 140.

In addition, the appearance of the external microphone may be changed in various ways in the future as long as the convenience of the user is guaranteed.

Figure 5:
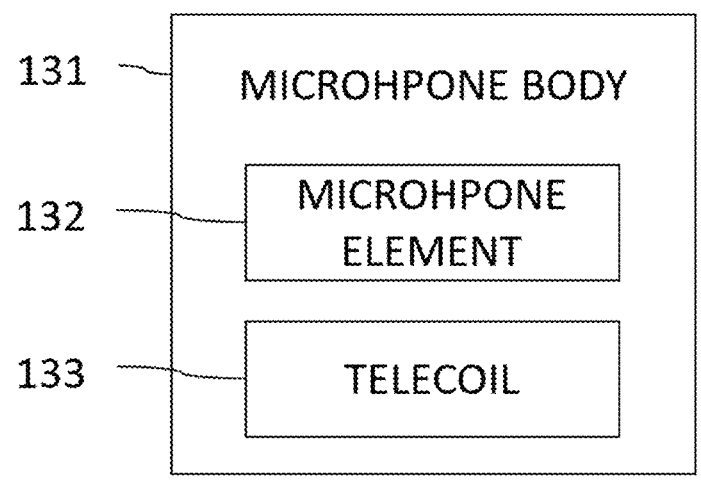
FIG. 5 is a diagram showing a configuration of the external microphone according to embodiments of the present disclosure.

FIG. 5 is a diagram showing a configuration of the external microphone according to embodiments of the present disclosure.

As shown in FIG. 5, the external microphone 130 may include a microphone body 131 implemented in a hook type or a terminal type and having an internal space formed therein and a microphone element 132 embedded in the microphone body 131.

In addition, the present disclosure additionally includes a telecoil 133 that receives a magnetic field signal generated from a telephone and converts it into sound, and the sound collecting operation may be performed using any one of the microphone element 132 and the telecoil 133. If so, the sound collecting operation may be performed by placing a phone terminal close to the ear instead of the external device body by means of the telecoil 133 provided to the external microphone 130, and as a result, the user may use the phone more naturally.

Figure 6:
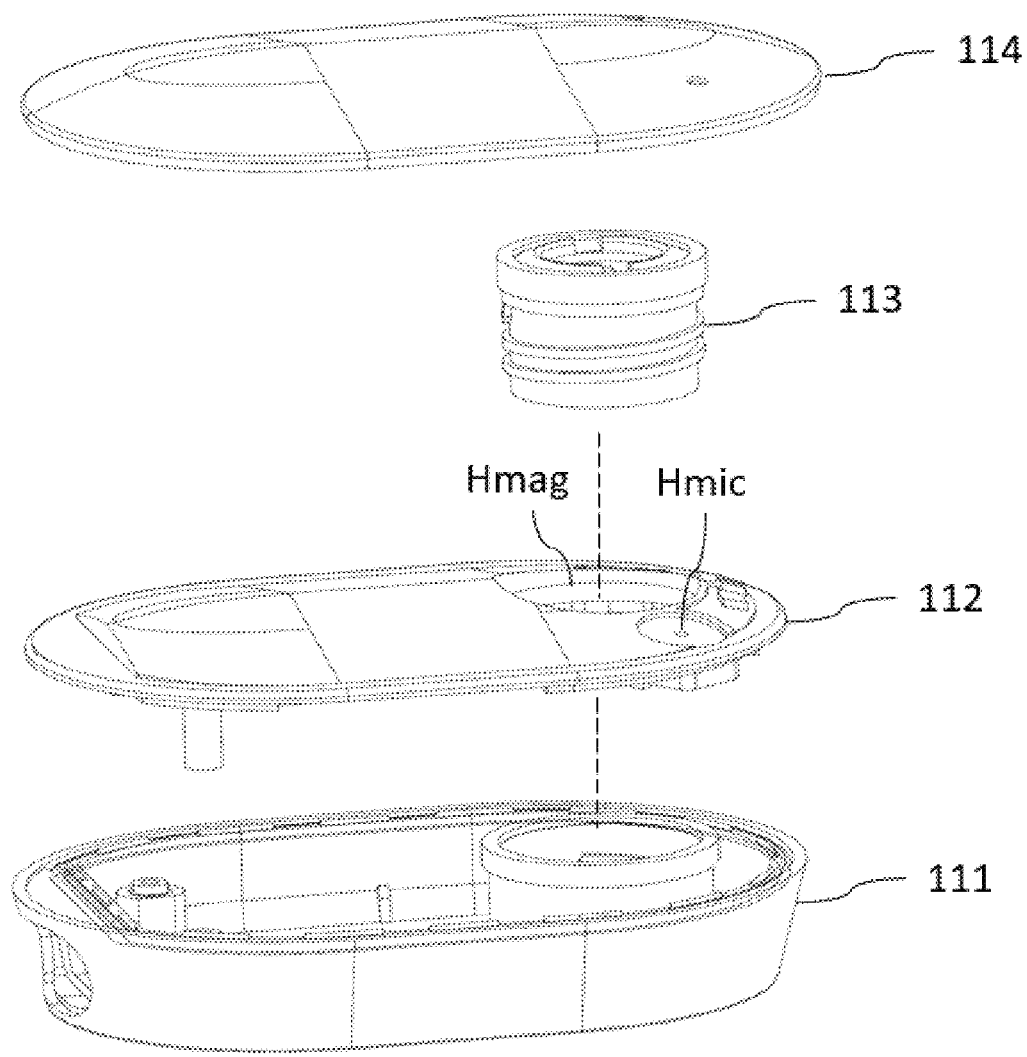
FIG. 6 is a diagram for illustrating a structure of the external device body according to an embodiment of the present disclosure.

FIG. 6 is a diagram for illustrating a structure of the external device body according to an embodiment of the present disclosure.

As shown in FIG. 6, the external device body 110 of the present disclosure may include a lower body 111 having an internal space for supporting components to be embedded, an inner cover 112 having a magnet insert hole (Hmag) and a microphone sound penetration hole (Hmic) and configured to cover an upper side of the lower body 111, a magnet 113 inserted into the magnet insert hole (Hmag) to adjust a height, and an outer cover 114 configured to entire cover and fully seal the inner cover 112 into which the magnet is inserted.

In the present disclosure, for the body cover, after the inner cover 112 and the outer cover 114 are prepared, the inner cover 112 is physically fixed to the body to protect a battery and circuit module therein, and the outer cover 114 is detachable from the body and has a metal material containing iron components so that the outer cover may be closely coupled to the body by the attraction between the metal material and the magnet.

The microphone sound penetration hole (Hmic) is formed based on the location of the internal microphone and gives a sound passage to increase the sound-receiving power of the microphone. At this time, the internal microphone 120 may be protected from dust by covering the microphone sound penetration hole (Hmic) with a replaceable filter net.

The magnet 113 and the magnet insert hole (Hmag) are helically coupled so that the magnet 113 may be coupled to or released from the body by rotation. In addition, by adjusting the height of the magnet 113, it is possible to adjust the coupling force with the internal implant.

In addition, although not shown in FIG. 6, a unit (for example, a display unit such as an LED) for notifying a remaining capacity of the battery provided in the power supply unit 160 may be additionally provided to the external device body 110.

According to an embodiment, since the display unit includes a plurality of LEDs, the light emitting state of the LEDs may be changed according to the remaining capacity of the battery.

For example, if the display unit includes three LEDs, the light emitting state of the LEDs may be controlled so that all of three LEDs are turned on when the remaining capacity of the battery is 100%, two LEDs are turned on when the remaining capacity of the battery is 50% or above, and one LED is turned on when the remaining capacity of the battery is 10% or above. In addition, the display unit may be provided to an inner surface (namely, a surface that contacts the skin) of the external device body 110 so that the display unit is not recognized from the outside when being worn by the user.

Figure 7:
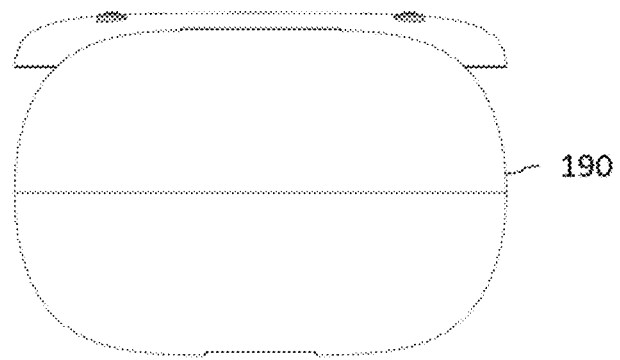
FIG. 7 is a diagram showing a charging cradle for supporting power charging of the external device body according to an embodiment of the present disclosure.
Figure 7:
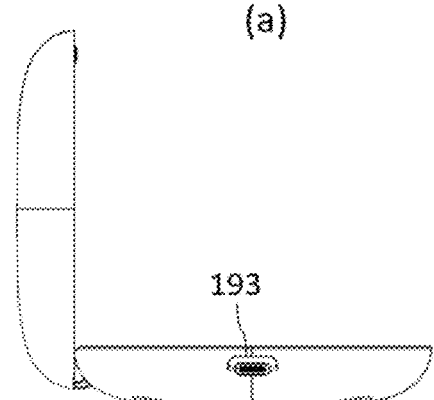
Figure 7:
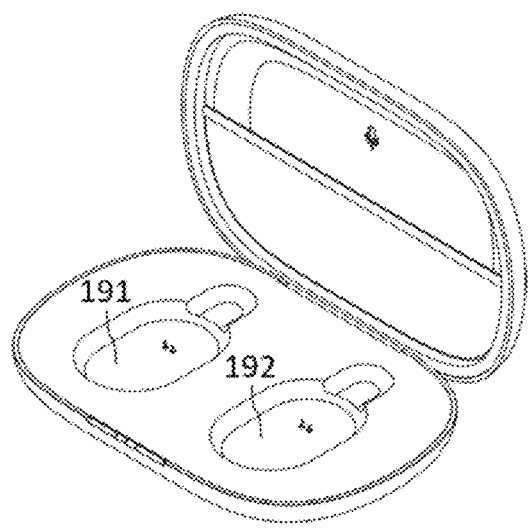

FIG. 7 is a diagram showing a charging cradle for supporting power charging of the external device body according to an embodiment of the present disclosure.

Referring to FIG. 7, a charging cradle 190 of the present disclosure includes two charging terminals 191, 192 capable of charging two external devices at the same time, a cradle connector 193 that supports connection with commercial power, and a power charging unit (not shown) that converts commercial power into a charging power and outputs the charging power to the charging terminals 191, 192, respectively.

Accordingly, if the user places the external device body 110 on the charging cradle 190 so that the charging terminals 191, 192 are connected to the power supply unit 160 of the external device body 110, the power supply unit 160 starts charging the battery by using the charging power supplied through the charging terminals 191, 192.

The charging cradle 190 of the present disclosure may also further includes a display unit such as an LED to visually guide a remaining capacity of the battery for charging.

For example, the light emitting state of the LEDs may be controlled so that all of three LEDs may be turned on if the remaining capacity of the battery is 100%, two LEDs may be turned on if the remaining capacity of the battery is 70% or above, and one LED is turned on if the remaining capacity of the battery is 30% or above.

The present disclosure is not limited by the above embodiments and the accompanying drawings. It will be apparent to those skilled in the art that components according to the present disclosure can be substituted, modified and changed within the scope of the technical idea of the present disclosure.

What is claimed is:

1. A cochlear external device with an external microphone, comprising:
   an external device body configured to be attached to a side of the head of a user;
   an internal microphone embedded in the external device body to collect sound;

an external microphone located at the outside of the external device body to be attached around the ear of the user to collect sound;

a connection cable configured to connect the external microphone and the external device body in a wired manner; and a control unit embedded in the external device body to generate an output signal based on the sound collected by at least one of the internal microphone and the external microphone and transmit the generated output signal to a cochlear implant transplanter;

wherein the external microphone comprises:
  a microphone body provided in a hook type or a terminal type;
  a microphone element embedded in the microphone body to collect sound; and
  a telecoil embedded in the microphone body to collect sound instead of the microphone element.

2. The cochlear external device of claim 1, wherein the external microphone is provided in a hook type that hangs on the earflap of the user or in a terminal type that is attached around the ear of the user.

3. The cochlear external device of claim 1, wherein the connection cable is detachably attached to the external device body.

4. The cochlear external device of claim 1, further comprising:
  a power supply unit having a battery for performing a power charging/discharging operation and configured to generate and supply a driving power for the cochlear external device by using a battery charge power.

5. The cochlear external device of claim 1, further comprising:
  a contact sensor configured to sense whether the external device body is attached to the head of the user and notify the sensing result,
  wherein the control unit changes an operation mode according to the sensing result of the contact sensor.

6. The cochlear external device of claim 1, further comprising:
  a vibration sensor configured to sense a user touch pattern based on vibration and notify the sensing result,
  wherein the control unit changes an operation mode according to the sensing result of the vibration sensor.

7. The cochlear external device of claim 1, wherein the external device body comprises:
  a lower body having an inner space for supporting components to be embedded therein;
  an inner cover having a magnet insert hole and a microphone sound penetration hole and configured to cover an upper side of the lower body;
  a magnet inserted into the magnet insert hole and configured to have an adjustable height; and
  an outer cover configured to entirely cover and fully seal the inner cover into which the magnet is inserted.

* * * * *